(12) United States Patent
Hallin

(10) Patent No.: US 8,423,181 B2
(45) Date of Patent: Apr. 16, 2013

(54) TABLET DISPENSER SYSTEM

(75) Inventor: Cristian Hallin, Halmstad (SE)

(73) Assignee: Medicpen AB, Halmstad (SE)

( * ) Notice: Subject to any disclaimer, the term of this patent is extended or adjusted under 35 U.S.C. 154(b) by 251 days.

(21) Appl. No.: 12/595,514

(22) PCT Filed: Apr. 11, 2007

(86) PCT No.: PCT/EP2007/003215
§ 371 (c)(1),
(2), (4) Date: Mar. 31, 2010

(87) PCT Pub. No.: WO2008/125128
PCT Pub. Date: Oct. 23, 2008

(65) Prior Publication Data
US 2010/0211219 A1   Aug. 19, 2010

(51) Int. Cl.
*G06F 17/00* (2006.01)
(52) U.S. Cl.
USPC .............................. 700/237; 221/93; 221/123
(58) Field of Classification Search .................. 700/237; 221/93, 123
See application file for complete search history.

(56) References Cited

U.S. PATENT DOCUMENTS

| | | | |
|---|---|---|---|
| 4,911,372 A | 3/1990 | Uchida et al. | |
| 5,267,174 A | 11/1993 | Kaufman et al. | |
| 5,642,731 A * | 7/1997 | Kehr | 600/300 |
| 6,004,020 A * | 12/1999 | Bartur | 700/236 |
| 6,085,752 A * | 7/2000 | Kehr et al. | 128/897 |
| 6,327,570 B1 | 12/2001 | Stevens | |
| 6,332,100 B1 * | 12/2001 | Sahai et al. | 700/242 |
| 7,061,831 B2 * | 6/2006 | De La Huerga | 221/2 |
| 7,080,755 B2 * | 7/2006 | Handfield et al. | 700/244 |
| 7,107,122 B1 * | 9/2006 | Whyte | 700/241 |
| 7,269,476 B2 * | 9/2007 | Ratnakar | 700/236 |
| 7,347,341 B2 * | 3/2008 | Burggraf | 221/197 |
| 7,359,765 B2 * | 4/2008 | Varvarelis et al. | 700/237 |
| 7,831,336 B2 * | 11/2010 | Gumpert | 700/244 |
| 2002/0169635 A1 * | 11/2002 | Shillingburg | 705/2 |
| 2004/0039481 A1 | 2/2004 | de la Huerga | |
| 2005/0252924 A1 | 11/2005 | Pieper et al. | |
| 2006/0157491 A1 | 7/2006 | Whittle et al. | |

FOREIGN PATENT DOCUMENTS

| | | | |
|---|---|---|---|
| CA | 2066173 A1 | 3/1991 | |
| CA | 2060796 A1 | 2/1993 | |
| JP | 11216171 A | 8/1999 | |
| JP | 2001000508 A | 1/2001 | |
| SE | 515 202 | 6/2001 | |
| WO | 0032088 A1 | 6/2000 | |
| WO | WO 02/17850 A1 | 3/2002 | |
| WO | WO 03/073977 A2 | 9/2003 | |

* cited by examiner

*Primary Examiner* — Timothy Waggoner
(74) *Attorney, Agent, or Firm* — Capitol City TechLaw (57) ABSTRACT

A tablet dispenser and a magazine therefore, said tablet dispenser being configured to receive said magazine adapted to contain a tablet, and to release the tablet in a controlled way is provided. The tablet dispenser or the magazine comprises a control unit configured to monitor, send or receive tablet dispenser information to or from an external device. A system and use is also provided.

32 Claims, 5 Drawing Sheets

TABLET DISPENSER SYSTEM

FIELD OF THE INVENTION

This invention pertains in general to the field of a tablet dispenser. More particularly the invention relates to a tablet dispenser system comprising such a tablet dispenser. A tablet dispenser of this kind is disclosed in SE 515 202.

BACKGROUND OF THE INVENTION

It is known that a dispenser for tablets is put into use in, for example, the dosing of medicines. In such instance, a dispenser for tablets has been provided by the present inventors, which tablet dispenser comprises a housing containing a container in the form of a tube formed to accommodate the tablets, which are to be located in the container. These tablets are stacked in said container to thereafter be delivered by a delivering mechanism to the user of the dispenser. A tablet dispenser of this kind is disclosed in SE 515 202.

A problem with a tablet dispenser of this kind is that the tablet dispenser only is suitable for one kind of tablet, i.e. a tablet of a certain size and proportion, corresponding to the size of the container. Thus, the user needs to change dispenser when he/she needs to change medicament, which new medicament comes in the form of a tablet with a different size and proportion than the original tablet. Also, different tablets do not only have different sizes in respect of surface area but also in respect of heights. This provides a further problem in respect of the output mechanism of the tablet dispenser. An advantage of utilizing a tablet dispenser is that it enables self-medication, which means that a patient himself/herself may administers his/her medication(s) by himself/herself without external help.

Currently, self-medication is often performed using a box comprising tablet compartments in a matrix, wherein e.g. each tablet compartment column defines an administration time, such as one row per week. Furthermore each row of the box may indicate a sub administration time, such as "Morning", "Lunch", or "Evening" administration, in the case of three tablet administrations per day are desired. However, there are several problems associated with self-medication using a box with tablet compartments explained above. Firstly, the tablet compartments may mistakenly be loaded with an incorrect amount and/or type of tablets that may result in adverse events for the patient. Secondly, even if the tablet compartments comprise the correct amount and type of tablets, the patient may still administer an incorrect amount or type of tablets, e.g. by choosing an incorrect tablet compartment comprising an incorrect amount and/or type. Moreover, as the tablets may be difficult to pick up from the tablet compartment, it may result in dropping the tablets, and thereby administering an incorrect amount and/or type of tablets.

Further problems associated with the use of a box comprising tablet compartments in a matrix or a tablet dispenser according to SE 515 202 are for example the facts that there is no indication provided to the physician in care of the user if the medication has been received by the user. Moreover there is no guarantee that the user has received the correct medication as tablet mistakably may be put in the wrong compartment of the box e.g. during preparation. Furthermore, there is no indication of when the user has received the correct medication.

Hence, an improved tablet dispenser, magazine, and system for such tablet dispenser or magazine would be advantageous.

SUMMARY OF THE INVENTION

Accordingly, the present invention preferably seeks to mitigate, alleviate or eliminate one or more of the above-identified deficiencies in the art and disadvantages singly or in any combination and solves at least the above-mentioned problems by providing a tablet unit, a docking device, a system, a medical workstation, and use according to the appended patent claims.

According to one aspect of the invention a tablet unit adapted to contain a tablet, and to release the tablet in a controlled way is provided. The tablet unit comprises a control unit configured to monitor, send or receive tablet dispenser information to or from an external device.

According to another aspect of the invention, a docking device for a tablet unit according to any one of the appended claims 1 to 50 is provided. The docking device is configured for transferring tablet dispenser information via wire or wireless to or from the external device or charge a battery of said tablet unit.

According to yet another aspect of the invention a system is provided. The system comprises a tablet unit according to any one of the claims 1 to 50, and external device being configured to receive or send tablet dispenser information or tablet level information from or to the tablet dispenser, and wherein the tablet dispenser further comprises a control unit configured to monitor, send or receive tablet dispenser information or tablet level information to or from the external device.

According to another aspect of the invention a medical workstation comprising a tablet unit according to any of appended claims 1 to 50, docking device according to appended claim 51, or system according to appended claim 52 is provided.

According to another aspect of the invention a use of the tablet unit according to any one of appended claims 1 to 50 for self-medication by a user, in clinical trials, or in hospital environment is provided.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

Several embodiments of the present invention will be described in more detail below with reference to the accompanying drawings in order for those skilled in the art to be able to carry out the invention. The invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments do not limit the invention, but the invention is only limited by the appended patent claims. Furthermore, the terminology used in the detailed description of the particular embodiments illustrated in the accompanying drawings is not intended to be limiting of the invention.

The following description focuses on embodiments of the present invention applicable to a dispenser, and in particular to a tablet dispenser configured to communicate and process tablet dispenser information. However, it will be appreciated that the invention is not limited to this application.

Tablet Dispenser

Figure 1:
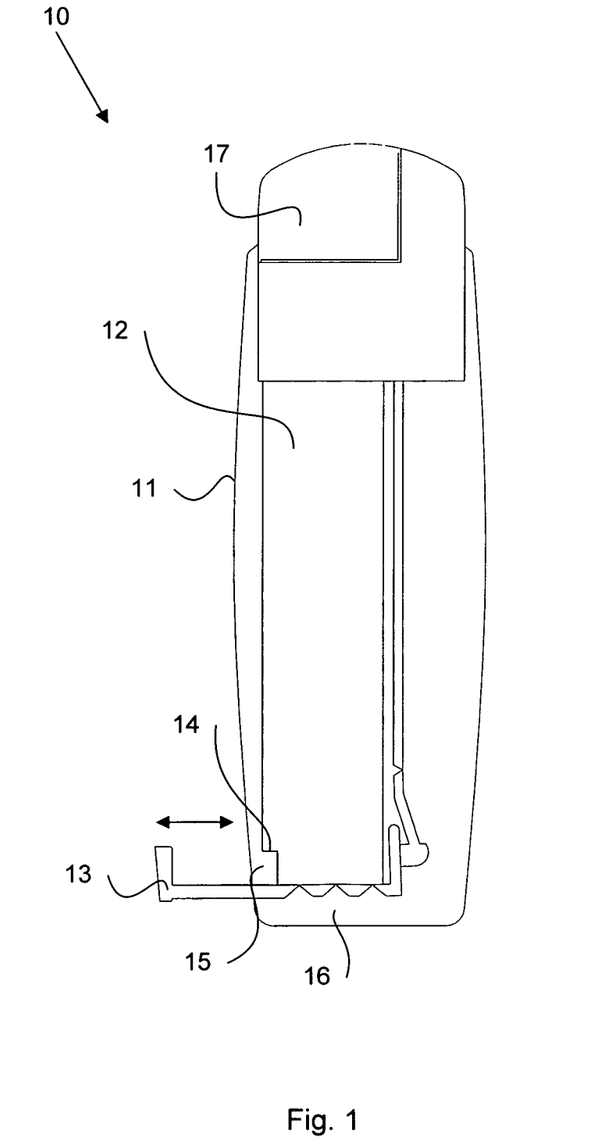
FIG. 1 is an illustration showing a tablet dispenser according to an embodiment.

In an embodiment, according to FIG. 1, a tablet dispenser 10 is provided. The tablet dispenser 10 comprises a housing 11. The housing 11 is of substantially rectangular cross section and wholly encloses a channel 12, adapted for receiving a tablet magazine 21 according to FIGS. 2a and 2b. This channel 12 may have the form of a tube of circular cross section or a cross section formed to accommodate said magazine 21, which is to be located in the dispenser. The tablet dispenser is also provided with an output mechanism, comprising an operating unit, such as a button. The operating unit may comprise a joint mechanism for transferring the movement on depression of a button to a reciprocating slide 13. The joint mechanism may include a first arm connected to the operating unit and a second arm, connected to the slide 13. The first arm may be connected to the operating unit by the intermediary of a first pivot and to the second arm by the intermediary of a second pivot. Furthermore, this tablet dispenser may comprise a lid or a closure member. The dispenser may also be provided with an abutment 14. This abutment 14 serves to support the magazine 21, such that the slide 13 is movable in a reciprocating movement transversely of the longitudinal direction of the magazine 21. Then, during use, the slide 13 slides through an output opening 15 at the bottom 16 of the tablet dispenser. The tablet dispenser may also be provided with a lid 17, which may be pivotably arranged at the top of the tablet dispenser.

Magazine

Figure 2A:
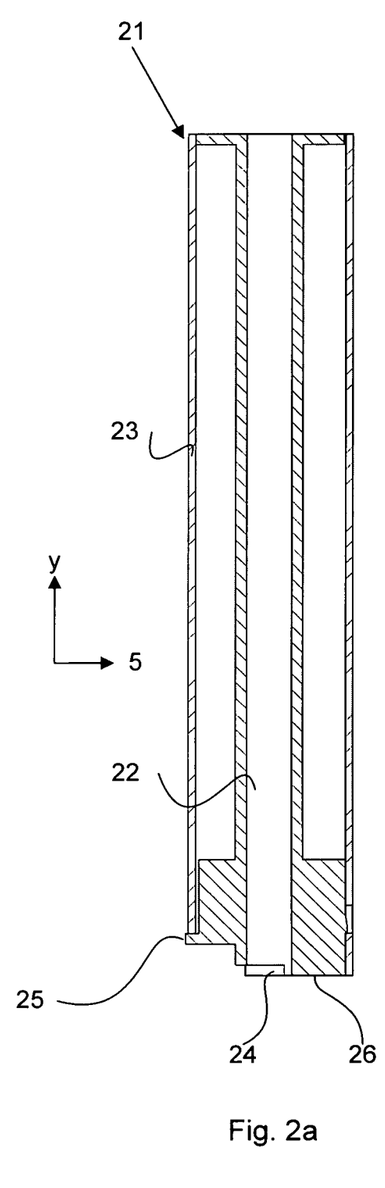
FIG. 2a is an illustration showing a magazine according to an embodiment.
Figure 2B:
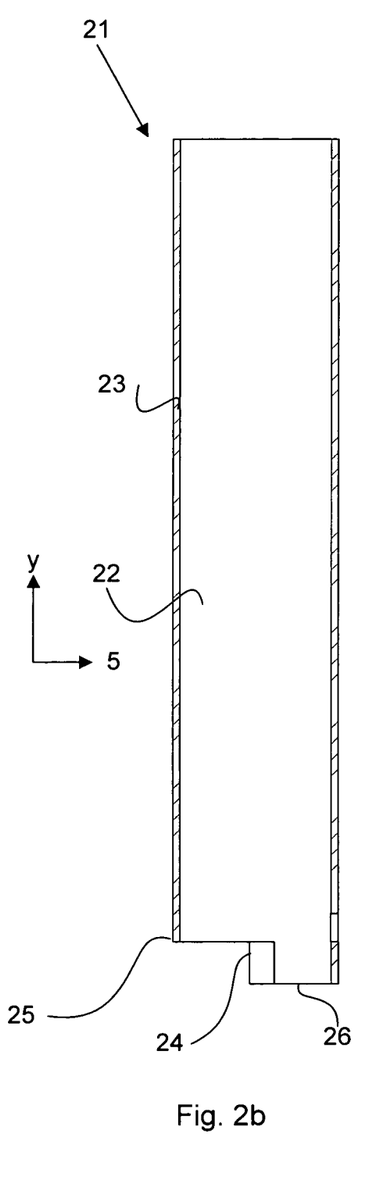
FIG. 2b is an illustration showing a magazine according to an embodiment.

In FIGS. 2a and 2b an embodiment of a tablet magazine 21 is illustrated in the x-y plane. The magazine 21, according to FIGS. 2a and 2b, has a tablet channel 22 and a cover 23. The tablet channel 22 has a first mouth in a first end of the magazine and an output mouth 24 in a second end of the magazine. Said second end is closest to the slide 13 of the tablet dispenser when the magazine is arranged in a tablet dispenser. This output mouth 24 comprises a mouth edge 25 and an end edge 26. Thus, the second end of the tablet channel may have an end edge 26 and a mouth edge 25, wherein the mouth edge 25 is located at a greater distance than the end edge 26 from the slide 13 when the magazine is arranged in the tablet dispenser.

Multiple Magazines

In an embodiment the tablet dispenser is configured to comprise several different tablet shapes and/or sizes (i.e. tablets having different heights, widths, and depths) simultaneously. In this embodiment the tablet dispenser is configured to comprise more than one channel 12, and hence more than one magazine, each capable of carrying a number of tablets of a specific type. This multiple magazine tablet dispenser is particularly advantageous when a combination treatment utilizing several different drug tablets is required for treatment of the patient.

Combination treatments often prove to be advantageous and provide higher treatment efficacy than treatment with one medication type alone. However, current ways of administering tablets in combination treatments, i.e. different types and/or number of tablets, by self-medication are not sufficiently reliable as the selection is made manually, and hence the human factor may result in that an incorrect tablet type and number of tablets are chosen. To make the administration easier to the user the outlets of the multiple magazines may be connected into one combined outlet. Thus, the user only needs to receive the medication from one outlet, regardless how many tablets the user is to administer during each reception of medication. The tablet dispenser according to the present invention solves at least these problems.

Identity Unit

In an embodiment, each magazine of the tablet dispenser has an identity e.g. defining the amount and/or type of tablets comprised in the magazine. The identity of each magazine is configured such that a detector unit 521 in FIG. 5, e.g. optionally comprised in the tablet dispenser, may retrieve the identity of the magazine, optionally when the magazine is placed in a channel of the tablet dispenser. The detector unit 521 may also be comprised in en external device. The identity of a magazine may be comprised in an identity unit located or attached in a suitable location of the magazine. The detector unit is configured to forward the received identity to a control unit e.g. comprised in the tablet dispenser for further processing, such as converting the received signal to the amount and/or type of tablets comprised in the magazine.

The detector unit, e.g. by sending incident optical or acoustic waves on the identity unit, may initiate the readout of the identity of the identity unit. In other embodiments the identity unit per se may send, e.g. via electromagnetic waves, its identity to an external device e.g. comprising a detector unit. This means that the other devices than the tablet dispenser may retrieve the identity from the magazine. For example, the magazine may communicate its identity, such as information regarding tablet type, tablet numbers in magazine, to a monitoring system, e.g. located at the site for filling the magazine with tablets. The monitoring system may monitor which tablet types and numbers that are filled in the magazine, e.g. by connection to the tablet filling apparatus. The monitoring system in conjunction with the identity unit may be used to confirm that the correct tablets or tablet amount are placed in the magazine or that the correct identity unit is placed on the magazine based on the tablet type and/or tablet amount in the magazine.

In an embodiment the identity unit may be programmed to have a certain identity e.g. from a distance by subjecting the identity unit with a magnetic field. In this way each magazine will comprise a programmable identity unit.

The identity unit of the magazine may be a tag, suitable for optical readout by the detector unit, such as a printed bar code tag located in a suitable location of the magazine. In other embodiments the tag for optical readout is based on technology, such as infrared light, ultraviolet light or ordinary wavelengths. Hence, the tag may have different color, i.e. different wavelength spectrum, depending on the type of tablets comprised in the magazine.

In other embodiments the tag is suitable for acoustic readout by the detector unit such as via ultrasound.

In an embodiment the identity unit is a geometrical hole or object provided on the magazine cover 23, and is enabling optical or acoustic readout.

Figure 3A:
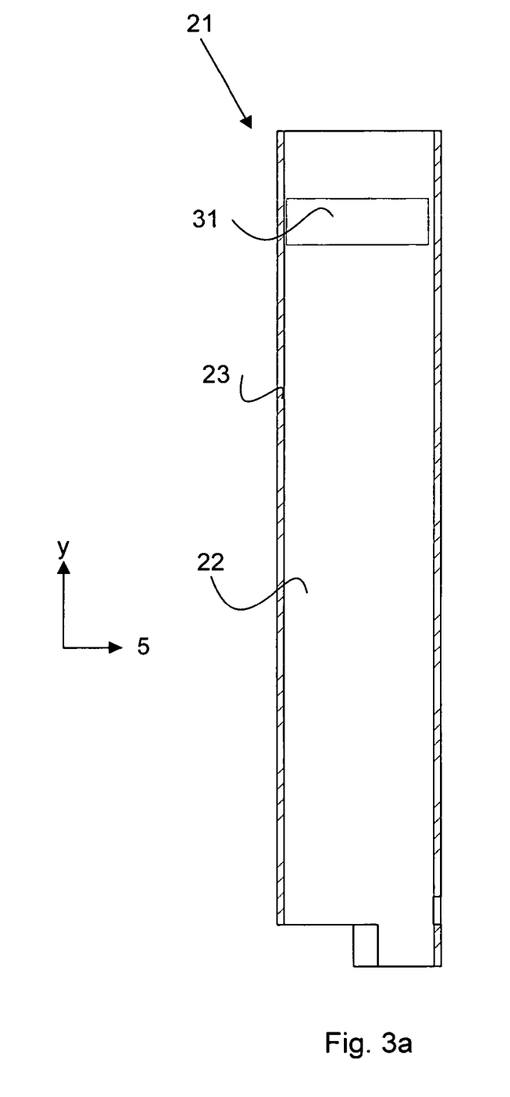
FIG. 3a is an illustration showing a magazine according to an embodiment.
Figure 3B:
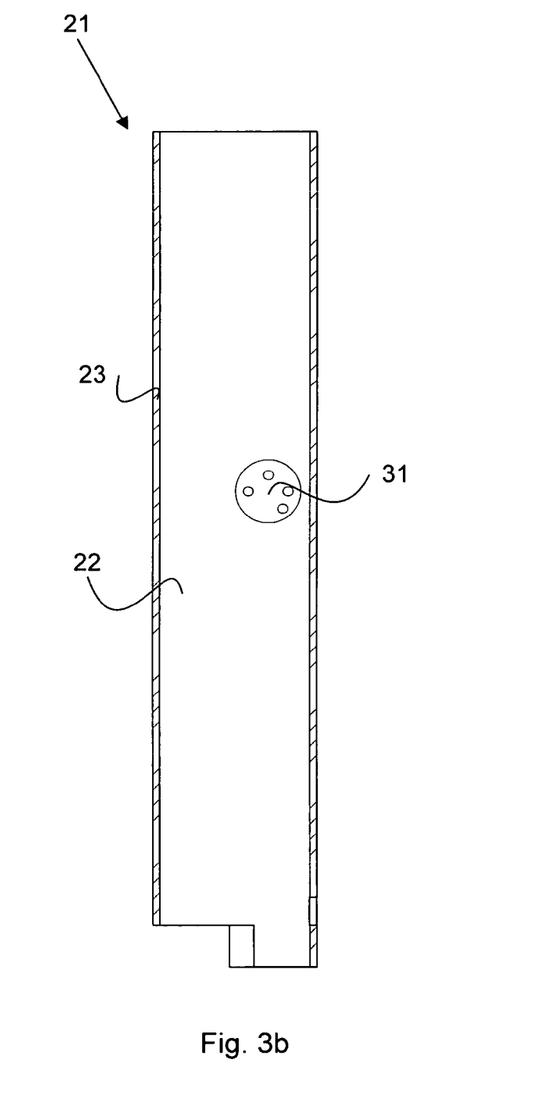
FIG. 3b is an illustration showing a magazine according to an embodiment.

In an embodiment, according to FIG. 3a, the identity unit 31 is located on/or in the cover 23 of the magazine 21. The location of the identity unit of the magazine when placed in a channel of the tablet dispenser may be located adjacent the detector unit that may be provided in close proximity to the channel and aligned with the identity unit. Hence, in other embodiments the location of the identity unit 31 may be anywhere on the magazine surface, such as illustrated in FIG. 3b, with an identity unit being comprised of circular indentations for either optical or acoustic readout.

By having one detector unit for each channel of the tablet dispenser the control unit is capable of controlling which tablet type belongs to which channel, and in this way enabling a correct amount of tablets from each magazine to be released in accordance with the dosage plan.

In other embodiments the identity unit is configured to communicating the identity of the magazine to the detector using a suitable technology, such as, but is not limited to: wire, Ethernet, WLAN, Bluetooth, Radio Waves, 3G, USB, GSM, GPRS, ADSL, Modem, Electrical Power Cables, Transponder Technology, light of infrared, ultraviolet or ordinary wavelengths or ultrasound communication or any combination thereof. Depending of the technology used to provide the control unit with the identity of the magazine, correspondingly the detector unit, and identity unit utilizes the same technology. The choice of the technology used to provide the control unit with information regarding the tablet type comprised in a magazine is not limited by the present invention. Any means for communicating the identity of the magazine may be used.

In some embodiments the tablet dispenser size is adapted for being held in a hand of a user.

In some embodiments the identity unit further comprises at least one of the capabilities as the control unit. In some embodiments the identity unit comprises all of the capabilities of the control unit.

Control Unit

In an embodiment the tablet dispenser comprises a control unit that is configured to process tablet dispenser information for use internally or externally. Tablet dispenser information may e.g. be dosage plans comprising tablet administration time, tablet type, number of tablets, tablet dispenser configurations, alarms, firmware updates, tablet dispenser serial number, etc.

Dosage Plan

In an embodiment the tablet dispenser is adapted to utilize a patient individual dosage plan e.g. being developed by the attending physician. Depending on the disease or disorder of the patient to be treated different dosage plans may be used. The dosage plan is based on parameters concerning the planned treatment process of the patient. These parameters may optionally be time of administration events, tablet type at each administration event, and/or number of tablets at each administration event, administration routes etc.

For a tablet dispenser containing one magazine, comprising tablets e.g. of the type A, a dosage plan defined for the administration times $t_1$-$t_3$, may for e.g. be $t_1$: 3A (three tablets of type A), $t_2$: 2A (two tablets of type A), $t_3$: 1A (one tablet of type A). In some embodiments the dosage plan the number of tablets administered at each administration time is the same at each administration, e.g. such as 3 tablets of type A at each of the administration times $t_1$ to $t_3$.

For a tablet dispenser containing more than one magazine, such as three magazines, each comprising tablets e.g. of the types A, B, and C, a dosage plan defined for the administration times $t_1$-$t_3$, may for e.g. be $t_1$: 1A+1B+2C, $t_2$: 2A+1B+3C, $t_3$: 1A+2B. Hence, both the number of tablets and tablet types may be varied between each administration time of the dosage plan. Thus, this embodiment provides for combination treatment. This embodiment drastically reduces the risk of incorrect administration of tablets compared to current practice wherein each dosage of tablets manually has to be placed into the box comprising tablet compartments explained above. As this is manually performed in current practice, there is an impendent risk placing an incorrect number of each tablet type in each tablet compartment of the known box. Accordingly, this embodiment improves the safety and accuracy of tablet administration.

Tablet Dispenser Information

In some embodiments the tablet dispenser information comprises the patient individual tablet administration history registered by the control unit of the tablet dispenser. The patient individual tablet administration history enables the attending physician or health care personnel to have a complete overview over the patient's self medication. Parameters defined in the patient individual tablet administration history are e.g. tablet administration times, tablet types, tablet numbers, missed medications etc. By having access to the patient individual tablet administration history through the tablet dispenser the attending physician optionally remotely may confirm or monitor that the patient is taking his/her medicine according to his/her dosage plan. Moreover, the patient individual tablet administration history enables traceability, that may be used subsequently to explain or investigate optional arisen side effects, mortalities etc. Accordingly, the patient individual tablet administration history provides the attending physician or health care personnel with information that has been unable to retrieve up until now.

In another embodiment the tablet dispenser information may be optionally synchronized with the individual patient journal, which may be located on a central computer, such as a hospital server. This enables the patient individual tablet administration history to be integrated into the patient journal, which facilitates overall monitoring of the patient, and accordingly reduce the time spent on gathering patient individual information.

In some embodiments the tablet dispenser information may be received from or sent to an external device via a communication unit (not shown), or be programmed internally into the control unit. The external device may e.g. be another tablet dispenser, a central processor, or a magazine having an identity defining the tablets comprised in the magazine.

According to some embodiments the tablet dispenser information that may be sent from/to the tablet dispenser to/from an external device or comprises tablet level information. The tablet level information directly pertains to information regarding each tablet. For example, the tablet level information may be information sent from an external device regarding administration of the tablet of a certain type. In other embodiments, the tablet level information comprises information that is registered in the tablet dispenser memory each and every time a tablet is administered from the tablet dispenser. Accordingly, the tablet level information may be interpreted as a sub portion of the dosage plan. Hence, tablet level information contains information regarding each tablet only, as the dosage plan may contain information regarding a plurality of tablets, such as a plurality of tablet level information. An advantage of this embodiment is that each and every tablet may be controlled or registered individually, and this inter alia provides for increased tablet traceability and improved safety for the treated patient.

Clock

In an embodiment the control unit comprises an internal and/or external clock that is used in communication or synchronization with the dosage plan to be able to determine when it is time for the next administration of tablets. The clock may be any clock suitable for being provided in a circuit of the control unit. The external clock may e.g. be provided in the external device.

Memory

Figure 5:
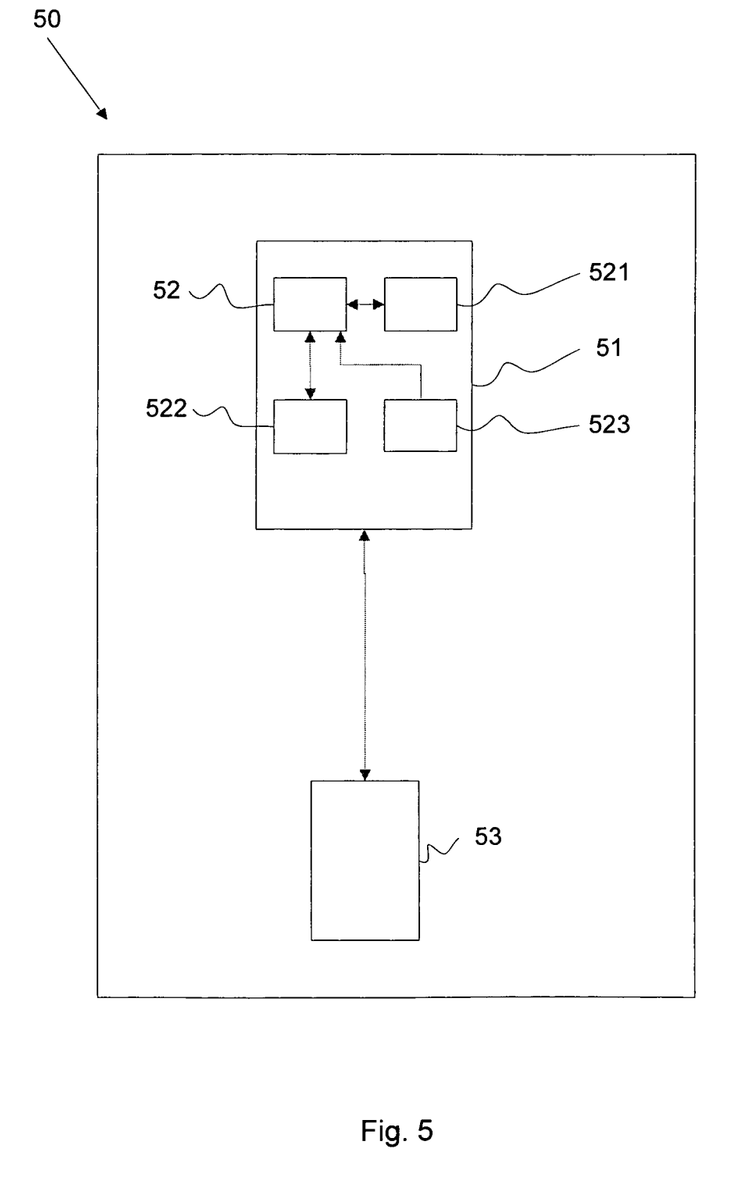
FIG. 5 is a block diagram of a system according to an embodiment.

In an embodiment the control unit further comprises a memory 522. The memory is configured to store information regarding all processed information of the control unit, such as dosage plans comprising the administration event times, amount and/or types of tablets for each administration time etc, that may be used to create the patient individual tablet administration history which enables traceability explained above. Moreover, the memory is capable of storing the identity of each magazine, or information from tablet number sensors regarding the amount of a dispensed tablet from each magazine at each administration event. Moreover, the memory is configured to store the patient individual tablet administration history, alarms etc.

In an embodiment the memory is locked for readout without having access to an encryption key. Thus is the memory cannot be manipulated, without having access to the encryption key. This embodiment is particularly useful when the tablet dispenser is used in clinical trials having strict regulations regarding the registered doses etc.

Alarm

In an embodiment the control unit of the tablet dispenser is configured to control an alarm unit 524 comprised in the tablet dispenser unit for producing an alarm signal for alerting the patient of a certain event. The alarm signal may e.g. be an acoustic or visual, such as an electromagnetic radiation based alarm signal. For an acoustic based alarm signal the alarm unit may comprise a loudspeaker, and the alarm signal may be characterized by a sound sequence, volume, time duration, etc., depending on the alarm event. In the case of an electromagnetic radiation based alarm signal the alarm unit may comprise a light radiation source, such as a Light Emitting Diode (LED) of any type, or display of any type for displaying information of the alarm event to the patient, and the alarm signal may be characterized by e.g. intensity, color, blinking, etc., depending on the alarm event.

In some embodiments a combination of acoustic and visual alarm may be used for an alarm event.

In some embodiments the alarm unit is activated by means of the control unit when it is time for the patient to administer the tablet dosage in accordance to the tablet dosage plan established by the attending physician.

In some embodiments the alarm is activated as a reminder alarm if the patient has not yet administered the tablets according to the dosage plan. The reminder alarm may be set to activate at predetermined time(s) after the original time for tablet administration alarm. Any predetermined time may be used, such as, but not limited to: 2, 5 min, 10 min, 20 min, 30 min, 60 min, etc.

In some embodiments the alarm signal is used for indicating status of the tablet dispenser, such as time left before battery depletion ("Change/charge battery"), magazine status such as time left before empty magazine etc. The alarm signal may be visualized using a display provided on the table dispenser e.g. for presenting a text or graphical message to the user. For example, a message could "Magazine No. 3 almost empty" or "Replace magazine No 2".

In some embodiments a tablet level indicator is presented in the tablet dispenser display to visualize the remaining number of tablets left in a magazine. In some embodiments the tablet level indicator is configured visualize the number of administrations left before a magazine has to be replaced. The tablet level indicator may e.g. be presented in the display in the display idle mode (mentioned in greater detail below).

In some embodiments the alarm unit is configured to send an alarm signal to an external device, such as a computer, mobile phone, email server, etc. Hence the alarm unit may utilize any technology for sending information, such as, but not limited to, wire, Ethernet, SMS, MMS, WLAN, Bluetooth, Radio Waves, 3G, USB, GSM, GPRS, ADSL, Modem, Electrical Power Cables, Transponder Technology, light of infrared, ultraviolet or ordinary wavelengths or ultrasound communication or any combination thereof. An advantage of this embodiment is that the attending physician or health care personnel may monitor the patient remotely, e.g. by being alerted when the patient has not taken his/her medication according to the dosage plan. This feature also improves the patient's safety, as the alarm signal may be used to alert the physician or health care personnel that the patient may be incapable of taking his/her medication, perhaps due to an accident, such as a fall, or a medical condition, such as a stroke or heart attack, cerebral haemorrhage, etc. Hence, the external alarm signal may be used as a quick and reliable tool to alert that the patient is unable to take his/her medication.

In a practical implementation, the health care personnel may try to contact the patient after receiving the external alarm signal In an embodiment the alarm signal sent to the external device may be activated after a predetermined number of reminder alarms has been activated such that no alarms to the external device are sent unnecessarily. In this way a patient has a predetermined time between the first alarm indicating time for administration and the last reminder alarm(s) to take his/her medication before an external alarm is sent to the external device.

In an embodiment an alarm signal is activated if the control unit detects that an inserted magazine does not contain the correct type of tablets for the dosage plan. For example, if the dosage plan, requires both tablets of type A and B, and if the only magazines inserted into the tablet dispenser contains tablets of type A, this alarm signal will be activated. Moreover, the display may present that a magazine comprising tablets of type B, has to be inserted into one of the channels provided in the tablet dispenser. This type of alarm provides for increased patient safety as only the correct type and amount of tablets will be administered.

In some embodiments, when at least one of the required tablet types are missing, it is possible to administer the remaining part of the medication, as long as this is approved by the dosage plan. Accordingly, one parameter of the dosage plan may concern the possibility to administer a part of the medication of each administration event, if one or more types of tablets being part of the medication are missing. Under certain circumstances it may be better for the patient to receive a part of the medication than no medication at all. However, in other circumstances this may have the opposite effect, and put the patient at risk. Hence, the feature of administering only a part of the medication according to the dosage plan may advantageously be integrated as a part of the dosage plan. This embodiment further improves the patient safety.

Tablet Dispensing Control

Figure 4:
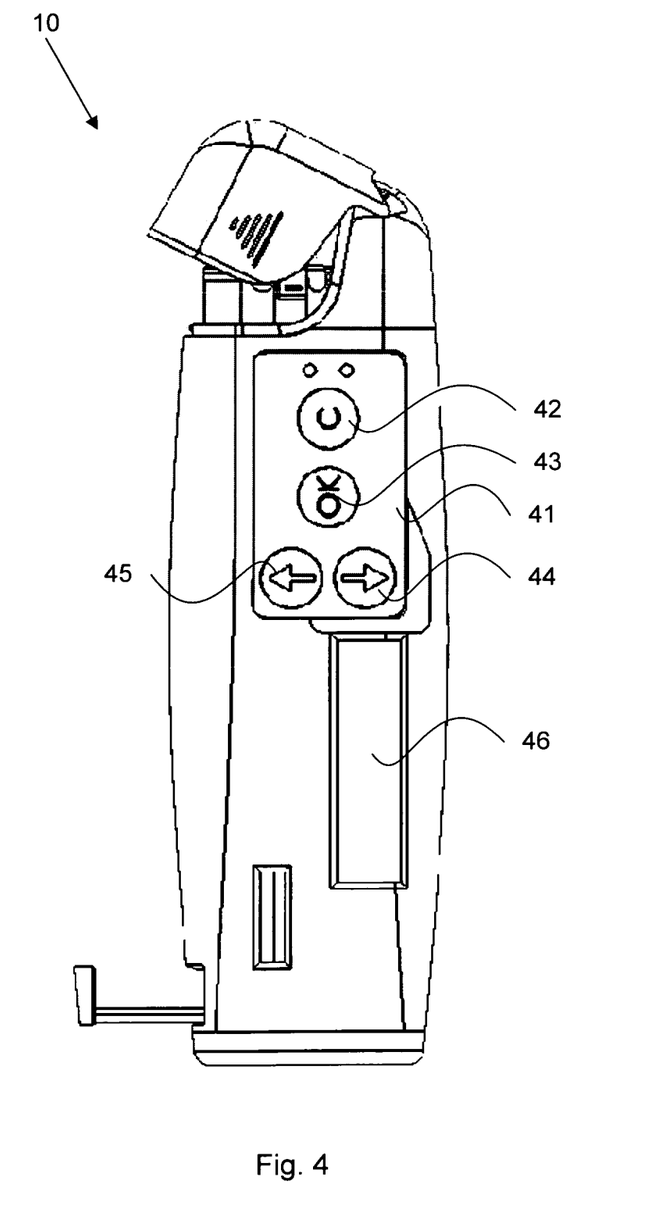
FIG. 4 is an illustration showing a tablet dispenser according to an embodiment.

FIG. 4 illustrates an embodiment of the tablet dispenser comprising a keypad or button set 41. The button set 41 according to this embodiment may e.g. comprise four buttons. One button may function as an "OK"-button 43, i.e. to confirm that a certain operation or setting should be performed. The "OK" button may also be used to enter the menu system of the tablet dispenser, which could be presented on the display 46. The button set 41 may also comprise a "clear" or "back" button 42 e.g. for enabling going back one step in the tablet dispenser menu system, to clear an input made e.g. by the buttons, or to jump back to the initial display mode, i.e. idle display mode wherein the display not presents the menu, but e.g. the time, battery status etc. Moreover the button set 41 may comprise one or more navigation buttons 44, 45, for enabling navigation throughout the menu system, or for use to manually input parameters, characters, or numbers e.g. corresponding to the to the dosage plan, tablet dispenser settings (time etc, energy save modes, toggling light on/of for the LED display etc.), or to input a message that could be sent optionally by wireless communication to the attending physician or health care personnel via the control unit. Moreover the button set may be used to display certain desired functions on the display, such as number of administration events left for each magazine before replacement is required, etc. Any configuration of buttons may be used in the tablet dispenser according to some embodiments in order for a user or health care personnel to monitor, or configuring the tablet dispenser. Moreover the button set may be used for receiving or sending messages between the tablet dispenser and an external device.

In an embodiment the tablet dispenser is configured to dispense a complete correct amount and/or type of tablets, in accordance with the dosage plan, by pushing a button, e.g. "OK" button 43, of the tablet dispenser button set. When, the tablet dispenser comprises more than one magazine combination it is possible to release the correct amount and/or types or tablets with only one push at the button. By utilizing this embodiment the risks of incorrect tablet administrations are drastically reduced. Moreover, it facilitates the self-medication of the patient, e.g. in terms of time-efficiency.

Throughout the present application the term "registered tablet administration" refers to the registration performed by the control unit of the tablet dispenser when the user press the button 43 to activate the tablet dispensing mechanisms to administrating the tablet dosage. The registered tablet administration may be a part of the patient individual administration history, In an embodiment a button, such as button 43, is connected to the control unit for enabling the control unit to register the time at which the button 43 is pushed, and accordingly the time when a tablet administration is delivered from the output opening 15 by the tablet dispenser output mechanism, into the control unit memory. Optionally together with additional tablet dispenser information, such as the amount and/or type of the tablets released, in connection to the push of the button 43, the registered push button time may be used in the control unit to create the patient individual tablet administration history, explained above.

In an embodiment the control unit is configured such that the dispensing of the next administration of tablets, is only possible when the tablet dispenser indicates, e.g. via alarm, that it is time for administration and the button 43 is pushed. Hence, if the button 43 is pushed before the time of next administration according to the dosage plan, no tablets will be released. Consequently, if the button 43 is pushed after the planned administration time the planned dosage of tablet will be dispensed from the output mechanism via the output opening 15. This embodiment is particularly advantageous to ensure that the medication is taken at the administration time defined in the dosage plan. Particularly, this embodiment may be useful for elder patients or patient incapable of remembering if they already have taken the tablets according to the last previous administration time. Moreover, this embodiment provides for alerting the patient when it is time for the next administration of tablets, which facilitates the self-medication.

In an embodiment the tablet dispenser unit comprises at least one tablet sensor 523, in FIG. 5, configured to count the number of tablets administered at each administration. For a tablet dispenser comprising multiple tablet magazines one tablet sensor may be located adjacent each magazine to register the number of tablet from each magazine (e.g. comprising different tablet types) that is administered at each tablet administration. Any technology enabling counting objects may be used in the tablet sensor. For example the tablet sensor may utilize an IR sensor to detect passing tablets. In other embodiments the tablet sensor utilizes optical imaging or acoustic imaging to detect the number of tablets either passing the tablet sensor during administration or the tablets left in the magazine after administration. The tablet sensor may function as a safety measure to ensure that the correct type and/or amount of tablets are administered correctly according to the dosage plan. If e.g. an incorrect type or amount of tablets is detected, the tablet sensor information may be used to activate an alarm signal or optionally graphical text information on the tablet dispenser display, for alerting the patient that an error has occurred. Moreover this alarm signal may prevent the patient of inserting the incorrect amount or type of tablets into his/her body via the administration route that may be defined in the dosage plan. The tablet sensor may also provide the control unit with the amount of tablets released from the corresponding magazine, in order to be able to calculate the time before the magazine will be empty and should be replaced, according to the following description.

In some embodiments the identity unit of the magazine is configured to provide the control unit with information regarding the number of tablets originally comprised, i.e. before use, in the magazine. By registration of the number of tablets, e.g. by using the tablet sensor in accordance with the dosage plan, for each magazine and administration event, it is possible to calculate the remaining amount of tablets in each magazine. Moreover, in accordance with the dosage plan, it is possible to calculate when it is time to replace each magazine with a new magazine containing tablets. This information may be presented, e.g. in the display 46 comprised in the tablet dispenser, to a patient. This embodiment is particularly advantageous to enable increased degree of mobility of the patient, as no additional magazines have to be carried along unnecessarily.

In another embodiment the tablet dispenser comprises a spring e.g. extending at least partly inside a magazine 21, arranged in said tablet dispenser, to thereby rest against a pushing member. This pushing member may then perform a pushing action on the tablets comprised in the magazine, wherein the length of the spring and the spring force may be used to indicate the number of tablets left in the magazine. By providing the spring with a pressure sensor, or spring length sensor, connected to the control unit the number of tablets left in the magazine may be calculated, when information is available regarding the tablet type, e.g. retrieved by the identity unit of each magazine. In a tablet dispenser comprising no tablet sensors, the spring and the identity unit may still be able to calculate the amount of tablets released from the magazine at each administration, by comparing the number of tablets in the magazine before and after the administration. The spring may be used as a replacement for the tablet sensor, or in conjunction with the tablet sensor to provide an even more accurate and reliable tablet dispenser.

In an embodiment the tablet dispenser comprises a display 46 for displaying tablet dispenser information to a user. The display may e.g. be used to alert the patient visually that it is time for medication, or present status of the tablet dispenser device, such as battery status, magazine status, etc. Optionally the display is based on Light Emitting Diode technology, such as Polymer Light Emitting Diode technology, or LCD-technology, such as a graphical LCD display. Optionally the display may have touch screen capabilities.

External Device—Central Processor Unit

In an embodiment the external device is a central processor unit e.g. centrally located at the health care center. The external device is configured to receive and/or send tablet dispenser information from or to the tablet dispenser. Received information by the external device may be patient individual tablet administration history, alarm signals, etc.

In an embodiment the control unit is configured to receive sent information from the external device. This information may e.g. be firmware updates, updates of dosage plans, messages to the patient that will be displayed in the display of the tablet dispenser, etc. The control unit then processes the sent information and performs the correct task involved, such as updates the firmware of the tablet dispenser.

External Display

In an embodiment, an external display is provided for monitoring, controlling, sending, and/or receiving information sent between at least one tablet dispenser and the central processor is provided. For example, in a hospital environment, the external display, such as a touch screen display, may be used to display of the geographical location of a tablet dispenser, alarm signals etc. If one tablet dispenser per treatment bed is provided, by receiving the tablet dispenser serial number, which may be comprised in the tablet dispenser information, the location of a certain tablet dispenser may be presented using the graphical user interface. This feature may be possible by manually registering which bed contains to which tablet dispenser. In some embodiments the external device is an external display.

In an embodiment, in the case an alarm signal is sent from a tablet dispenser unit located on e.g. level 6, room 2, bed 3 in a hospital, the external display may present the corresponding tablet dispenser location together with the alarm signal character. In this way several patients may be monitored simultaneously, and centrally using the same external device. This will reduce costs and unnecessary workload of the health care personnel.

In another embodiment, the tablet dispenser may comprise a General Positioning System unit, capable of sending its geographical location to the external device or external display.

Docking Device

In an embodiment the tablet dispenser may be connected to a docking device for transferring tablet dispenser information via wire or wireless to the external device, such as a personal computer. As an example, an attending physician or health care centre, without having access to the central processor, may still retrieve/send information from/to the tablet dispenser, which may be very advantageous and be used as a safety measure, e.g. if no wireless communication is available. A condition for this embodiment to function is thus that the tablet dispenser is physically connected to the docking device, and thus the patient must bring the tablet dispenser unit to the location of the docking device, such as to the health care centre. The docking device may also be used to charge the tablet dispenser battery when the battery is capable of recharging. Any battery may be used in the tablet dispenser according to some embodiments.

In an embodiment, according to FIG. 5, a system 50 is provided. The system comprises a tablet dispenser 51 configured to receive a magazine adapted to contain a tablet, and to release the tablet in a controlled way. The system further comprises an external device 53 being configured to receive or send tablet dispenser information from or to the tablet dispenser 51. The tablet dispenser 51 further comprises a control unit 52 adapted to monitor, send or receive tablet dispenser information to or from the external device 53. The tablet dispenser may optionally comprise a detector unit 521 for enabling identification of the magazine, a memory 522, a tablet sensor 523, and/or an alarm unit 524 according to the embodiments disclosed above.

The control unit may be any unit normally used for performing the involved tasks, e.g. a hardware, such as a processor with a memory. The processor may be any of variety of processors, such as Intel or AMD processors, CPUs, microprocessors, Programmable Intelligent Computer (PIC) microcontrollers, Digital Signal Processors (DSP), etc. However, the scope of the invention is not limited to these specific processors. The memory may be any memory capable of storing information, such as Random Access Memories (RAM) such as, Double Density RAM (DDR, DDR2), Single Density RAM (SDRAM), Static RAM (SRAM), Dynamic RAM (DRAM), Video RAM (VRAM), etc. The memory may also be a FLASH memory such as a USB, Compact Flash, SmartMedia, MMC memory, MemoryStick, SD Card, MiniSD, MicroSD, xD Card, TransFlash, and MicroDrive memory etc. However, the scope of the invention is not limited to these specific memories.

In an embodiment the tablet dispenser, external device, or external display may be comprised in a medical or clinical workstation or medical or clinical system.

The tablet dispenser according to some embodiments may be used for home use self-medication, in clinical trials, hospital environments, etc.

The tablet dispenser and the magazine according to the various embodiments may also be employed for other types of objects, which are stackable in a suitable manner.

The invention can be implemented in any suitable form including hardware, software, firmware or any combination of these. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific embodiments, it is not intended to be limited to the specific form set forth herein. Rather, the invention is limited only by the accompanying claims and, other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc. do not preclude a plurality.

The invention claimed is:

1. A tablet unit for self medication of a combination of at least two tablet types, said tablet unit being configured to receive at least two magazines, each magazine being arranged to include a number of tablets of one tablet type, said tablet unit comprising:
 a control unit configured to:
  receive a dosage plan from an external device; and
  based on the dosage plan release a correct number of each tablet type from each of the at least two magazines when a button provided on the tablet unit is pushed;
 wherein the tablet unit size is adapted for being held in a hand of a user.

2. The tablet unit according to claim 1, wherein at least one magazine is provided with an identity comprised in an identity unit configured to at least define the tablet type contained in said at least one magazine.

3. The tablet unit according to claim 2, wherein the identity unit is configured to at least define the tablet number contained in said at least one magazine.

4. The tablet unit according to claim 2, wherein the identity unit is configured to send the identity to the external device.

5. The tablet unit according to claim 2, wherein the tablet unit or the external device further comprises a detector unit being configured to retrieve the identity of the identity unit of each magazine.

6. The tablet unit according to claim 5, wherein the identity unit is a tag suitable for optical or acoustic readout by means of the detector unit.

7. The tablet unit according to claim 5, wherein the identity unit is a geometrical hole or object provided on the magazine being suitable for optical or acoustic readout by means of the detector unit.

8. The tablet unit according to claim 1, wherein the external device is another tablet unit.

9. The tablet unit according to claim 1, wherein the external device is a central processor.

10. The tablet unit according to claim 1, wherein the at least two magazines contain different tablet shapes, types or sizes, respectively.

11. The tablet unit according to claim 1, wherein said control unit is configured to receive or send tablet dispenser information containing at least one of: a dosage plan; a tablet unit configuration; an alarm; a firmware update; and a tablet unit serial number, or a tablet level information, from or to the external device.

12. The tablet unit according to claim 1, wherein said control unit is configured to process tablet dispenser information containing at least one of: a dosage plan; a tablet unit configuration; an alarm; a firmware update; and a tablet unit serial number, or a tablet level information.

13. The tablet unit according to claim 1, wherein said dosage plan is based on parameters concerning a planned treatment process of a patient, said parameters pertaining to at least one of: a time of administration event; a tablet type at each administration event; a number of tablets for each type at each administration event; and an administration route.

14. The tablet unit according to claim 1, wherein said control unit is configured to register all tablet administration events to provide a patient individual tablet administration history providing an overview of the tablet administrations or missed tablet administrations from said tablet unit.

15. The tablet unit according to claim 11, wherein said control unit is configured to synchronize said tablet dispenser information or said tablet level information with the external device.

16. The tablet unit according to claim 1, wherein said control unit comprises an internal clock or an external clock unit for use in conjunction with said dosage plan to determine a time for a tablet administration event.

17. The tablet unit according to claim 1, wherein said control unit further comprises a memory for storing processed information of said control unit, or tablet dispenser information, or tablet level information.

18. The tablet unit according to claim 17, wherein said memory is locked for readout by means of an encryption key.

19. The tablet unit according to claim 1, wherein said control unit is configured to control an alarm unit comprised in the tablet unit for producing an alarm signal for alerting a patient.

20. The tablet unit according to claim 19, wherein said alarm signal is an acoustic based or an electromagnetic radiation based alarm signal.

21. The tablet unit according to claim 1, further comprising a display for presentation of tablet dispenser information or tablet level information to a user.

22. The tablet unit according to claim 21, wherein said button is further configured to control
 navigation in a tablet unit menu system,
 tablet unit settings,
 manual input of parameters, characters, or numbers,
 display settings, or
 input of a message.

23. The tablet unit according to claim 1, further comprising a tablet sensor configured to count the number of tablets administered at each administration for each magazine.

24. The tablet unit according to claim 1, wherein tablet dispenser information or tablet level information received from the external device is at least one of:
 a firmware update;
 an update of dosage plan; or
 a message that will be displayed in a display of the tablet unit.

25. The tablet unit according to claim 1, wherein the external device is a further magazine.

26. The tablet unit according to claim 25, wherein the further magazine is provided with an identity comprised in an identity unit configured to at least define the tablet type or the tablet number contained in said further magazine.

27. The tablet unit according to claim 1, further comprising a General Positioning System unit to send a geographical location to the external device.

28. A docking device for a tablet unit according to claim 1, said docking device being configured for at least one of
 transferring tablet dispenser information or tablet level information via wire or wireless to or from the external device, and
 charging a battery of said tablet unit.

29. A system comprising:
 a tablet unit according to claim 1;
 wherein the external device is configured to receive or send tablet dispenser information or tablet level information from or to the tablet unit; and
 wherein the control unit is configured to monitor, send or receive tablet dispenser information or tablet level information to or from the external device.

30. A medical workstation comprising at least one of a tablet unit according to claim 1, a docking device according to claim 28, and a system according to claim 29.

31. A method comprising:
 using the tablet unit according to claim 1 for self-medication by a user, in clinical trials, or in a hospital environment.

32. A tablet unit for self medication of a combination of at least two tablet types, said tablet unit being configured to receive at least two magazines, each magazine being arranged to include a number of tablets of one tablet type, said tablet unit comprising:
- a control unit configured to:
    - receive a dosage plan from an external device; and
    - based on the dosage plan release a correct number of each tablet type from each of the at least two magazines when a single button provided on the tablet unit is pushed only once;
- wherein the tablet unit size is adapted for being held in a hand of a user.

* * * * *